(12) United States Patent
Gulo

(10) Patent No.: US 8,357,336 B2
(45) Date of Patent: Jan. 22, 2013

(54) SAMPLE ENTRY DEVICE

(75) Inventor: Stefan Gulo, Riederhof (AT)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 1347 days.

(21) Appl. No.: 11/743,192

(22) Filed: May 2, 2007

(65) Prior Publication Data

US 2007/0282224 A1  Dec. 6, 2007

(30) Foreign Application Priority Data

May 2, 2006 (AT) .................................. A 748/2006

(51) Int. Cl.
  *B65D 81/00* (2006.01)
(52) U.S. Cl. ......... 422/430; 422/68.1; 422/50; 600/573; 600/300
(58) Field of Classification Search .................. 422/100, 422/430, 68.1; 600/576, 300
  See application file for complete search history.

(56) References Cited

U.S. PATENT DOCUMENTS

| | | | |
|---|---|---|---|
| 4,499,053 A | 2/1985 | Jones | |
| 5,151,184 A * | 9/1992 | Ferkany | ........................ 210/514 |
| 5,391,499 A | 2/1995 | Karkantis et al. | |
| 5,455,007 A | 10/1995 | Calvo et al. | |
| 5,837,203 A * | 11/1998 | Godec et al. | ................. 422/100 |

FOREIGN PATENT DOCUMENTS

| | | |
|---|---|---|
| DE | 3890175 C1 | 4/1994 |
| EP | 0297082 B1 | 12/1988 |
| EP | 0564439 A2 | 10/1993 |
| EP | 0452892 B1 | 3/1996 |
| EP | 1347282 A2 | 9/2003 |
| WO | 9821562 A1 | 5/1998 |

* cited by examiner

*Primary Examiner* — Christine T Mui
(74) *Attorney, Agent, or Firm* — Roche Diagnostics Operations, Inc.

(57) ABSTRACT

A sample entry device is provided comprising a single plug-in site for automated input of medical samples, typically samples of body fluids, or quality control media, from diverse sample vessels. Sample transport containers are provided in the entry device, each having a cannula that can be inserted both through an opening into an open sample vessel and through a penetrable lid element into a closed sample vessel, and the entry device is provided with guiding elements, which will grip the cannula of the sample transport container to guide and center the cannula before it is inserted into the sample vessel or punctures it.

16 Claims, 3 Drawing Sheets

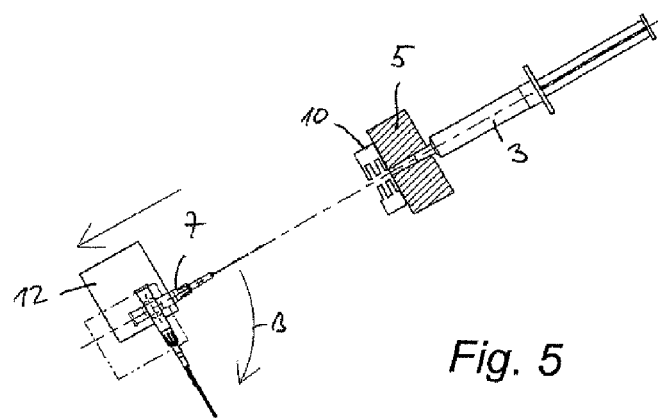
Fig. 5
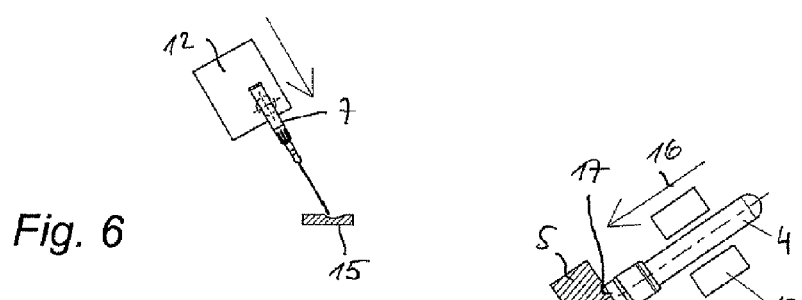
Fig. 6
Fig. 7
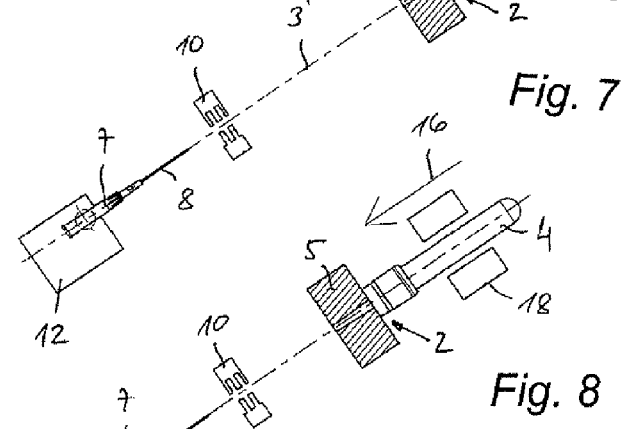
Fig. 8
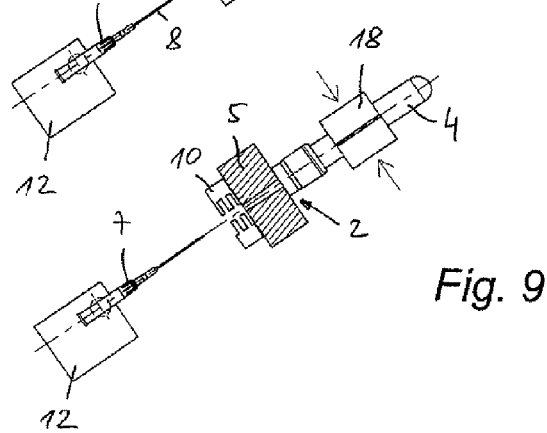
Fig. 9

SAMPLE ENTRY DEVICE

BACKGROUND OF THE INVENTION

The present invention relates to sample entry devices and, more particularly, to a sample entry device with a single plug-in site for the automated input of medical samples, typically samples of body fluids, or quality control media from diverse sample vessels.

Sample entry devices are known from medical laboratories, for example, where they may be used with blood analyzers for the analysis of whole blood, serum, plasma, or for other measurements of body fluids, such as liquor, pleura fluid, urine, etc. Some of these analyzers are designed for only one kind of sample vessel; they may for instance only permit sample input by means of a syringe.

For this reason the wish has often been expressed that sample entry devices be developed which should be suitable for sample input from diverse sample vessels, without requiring time-consuming adaptations.

In EP 0 297 082 an analyzer for samples of body fluids is disclosed, which has a rotatable docking disk, which in diverse rotational positions can be connected with a fitting of the sample feed line of the analyzer. Via this docking disk the sample can be entered, i.e., it is either aspirated by means of a peristaltic pump or injected into the sample input. The disadvantage of a sample entry device of this kind is that closed sample vessels such as so-called Vacutainers® or Monovettes® cannot be used, and that cleaning the sample input opening in order to avoid cross-contamination by sample residues is relatively difficult and costly.

A sample entry device similar to that of EP 0 297 082 is described in DE 38 90 175 C1. In that device a distributor disk is provided, which rotates about an axle and has a plurality of input elements positioned at equal distances relative to the axle, which elements may be connected to the media to be entered by means of suitable connectors. The distributor disk is held in the housing of the analyzer by means of a carrier shaft, the analyzer further being provided with a control unit for rotational and lifting motion of the distributor disk. In one rotational position the distributor disk has a slot, such that the sample input opening for introducing, the sample by means of a pipette or ac syringe is uncovered. The sample input device described in DE 38 90 175 C1 may thus be used to aspirate the sample from a capillary or to inject it by means of a syringe, with a conical opening being provided to receive and seal the capillary or the syringe, which opening is connected directly to the measuring cells of the analyzer via a rigid, gas-tight line. This entry device is not suited for another type of input preferred in laboratories, however. i.e., sample input from closed sample vessels, for instance Vacutainers® or Monovettes®.

In an entry device known from EP 0 564 439 A2 a flap swiveling around a fixed axle is provided for entering washing and reference media, which are fed to an elastic input element of the analyzer when the flap is closed. When the flap is open the input element can be freely accessed for aspiration from capillaries or injection by means of a syringe. The disadvantages mentioned above for EP 0 297 082 remain the same.

There are also known sample entry devices which permit aspiration of the sample from a syringe. There is a great variety of entry devices in which a swivelled input needle is provided, such that the diverse positions of the needle sample fluid tray be aspirated into the analyzer from diverse sample vessels. In this context U.S. Pat. No. 4,499,053 A should be mentioned, which describes a relatively complicated lifting mechanism with a guide link structure, the sample being aspirated either from a capillary or from a syringe. To this end the intake needle is provided with an intake element, which with its central orifice is axially guided on the intake needle and controlled by a link structure. By means of a handle on the link structure the intake needle may be tilted up from a rest position, in which it is connected with a fitting for a rinsing solution, to various other positions in which—guided by the link structure—the intake element assumes diverse positions along the axis of the intake needle. In one lift position the needle tip is completely exposed, such that the needle may be dipped into open sample vessels to aspirate the sample. In another lift position the needle tip is located within the central orifice of the intake element and a sample capillary may be inserted and held in the remaining open space of the central orifice. The sample may then be aspirated by the pump of the analyzer. Finally there is provided a further lift position, in which the intake needle assumes an essentially horizontal position and the intake element exposes a small piece of the needle tip. The cone of a syringe may now be slipped over the needle tip and pressed against, the outer face of the intake element, whereupon the sample may be injected into the analyzer. As a disadvantage it should be mentioned that the syringe is not supported by the entry device, and that the outer face of the intake element will provide only an insufficient seal, such that sample residues may contaminate the entry device.

A serious disadvantage of the entry device according to U.S. Pat. No. 4,499,053 A lies in the fact, however, that it is not possible to introduce samples from closed sample vessels.

In U.S. Pat. No. 5,391,499 A an entry system is described n which sample input is possible with the use of two different sample vessels, i.e., with a syringe (see FIG. 1) or with a sample capillary (see FIG. 2). By means of a rotatable element in the area of sample entry it can be ascertained automatically from the diameter of the sample vessel whether a syringe or a sample capillary has been inserted into the input orifice, and a different input program can be initiated for each type of input. The intake needle is either moved forward in longitudinal direction by means of a drive unit to penetrate into the syringe, or is retracted to make room for a capillary. A disadvantage of the entry system according to U.S. Pat. No. 5,391,499 A, which has to be rinsed with a washing solution before each new measurement, lies in the fact that it will not permit sample input from a Vacutainer®, for example.

It is further known in the art to use different adaptors for different sample vessels, which must be attached to the intake element of the analyzer or must be inserted into it. This will however call for increased manipulation efforts and will increase the risk of operator errors.

In the context of automated sample withdrawal from closed test tubes it is also known to puncture the stopper of the test tube by means of a robot mechanism at whose end a sharpened hollow needle is provided, and to withdraw the sample. In EP 0 452 892 B1, for instance, a device is described for sample withdrawal from open or closed vessels, whose needle can penetrate the sealing cap of a Vacutainers® but is apparently not made for insertion into the small-diameter opening of a syringe. As a further disadvantage this known sample entry device requires a special washing station for the needle.

Finally, from EP 1 347 282 A2 there is known a sample entry device with a stationary intake needle located on the sample entry side of the analyzer. The intake needle is provided with an elastic intake element which slides axially on the needle and has a conical input opening. Furthermore a holding element is provided, which is moveable relative to the intake element and can be shifted axially parallel to the needle, and which in a first position permits free access to the intake element and in a second position pieces a conical orifice for receiving a syringe above the intake element. In the first position of the holding element, in which the conical input opening of the elastic intake element is exposed, the sample may advantageously be aspirated from a capillary or injected by means of a syringe. In the second position, which is reached by a translational or rotational shift of the holding element starting from the first position, the holding element receives the syringe, which is placed above the intake needle and slipped over the intake needle, by a subsequent lifting motion of the holding element. Following this the sample may be aspirated from the interior of the syringe. Direct input of samples from closed sample vessels, such as Vacutainers® or Monovettes®, is not possible, however. Besides, the stationary intake needle has to be cleaned prior to each sample entry action.

SUMMARY OF THE INVENTION

It is against the above background that the present invention provides certain unobvious advantages and advancements over the prior art. In particular, the inventor has recognized a need for improvements in sample entry devices.

Although the present invention is not limited to specific advantages or functionality, it is noted that the present invention provides a sample entry device for medical samples, typically samples of body fluids, or quality control media, which enables samples to be drawn from diverse open or closed sample vessels, and that minimizes efforts for cleaning the entry device. The sample entry device is substantially contamination-free, such that there is no contact between sample and operator nor between the sample and the supporting elements of the sample vessels.

In accordance with one embodiment of the invention, a sample entry device is provided comprising a single plug-in site for the automated input of samples from at least two different sample vessels, at least one sample transport container, and guiding elements. Each sample transport container has a cannula, wherein the cannula is insertable through an opening into a first, open sample vessel and is also insertable through a penetrable lid element into a second, closed sample vessel. The guiding elements are configured to grip the cannula of the sample transport container prior to insertion or penetration of the cannula into the open or closed sample vessel to guide and/or center the cannula.

The sample transport containers can be provided in the sample entry device, each container having a hollow needle which may be inserted into the open sample vessel as well as into the sample vessel closed by a lid element which may be punctured. The guiding elements guide and/or center the hollow needle of the sample transport container before it is inserted Into or penetrates the sample vessel. Due to the use of guiding elements, which guide and in particular center and support the hollow needle, a sufficiently thin needle may be used, which on the one hand can be inserted into the small-diameter opening of the luer connection of a syringe and on the other hand can penetrate the lid of a Vacutainers® without bending or breaking. Typically the sample transport containers are furnished with a hollow needle (e.g., steel) sharpened as a cannula.

The guiding elements for the needle may be configured as active gripping elements or as passive guiding elements, e.g., in the form of a conical funnel.

Besides receiving the sample the sample transport container also serves to transport and transfer the sample to other functional units of the analyzer (for instance placing the sample onto a test strip, into reagent solutions, into measuring test tubes or transferring it to other internal sample transport systems).

The sample transport container which is typically designed for single use, has a body (e.g., plastic) with a hollow space for receiving the sample, which on the entry side is provided with a hollow needle (e.g., steel) sharpened as at cannula. The only contact of the sample in the entry device will be with the sample transport container, which is discarded after each sample input, thus completely eliminating the need for cleaning the entry device and avoiding any risk of cross-contamination in the device.

In a typical embodiment of the present invention, a plurality of sample transport containers are held in a storage space of the entry device, a gripping and swiveling mechanism being provided, which takes a sample transport container from the storage space, aligns it for sample withdrawal from the sample vessel, inserts it into the sample vessel and, after the sample has been withdrawn and transferred to a measuring area, either discards it into a separate waste container or returns it to the storage space. In the latter case the used sample transport containers are returned to their original storage place and marked as used by the transport mechanism.

The sample entry device is provided with a retracting mechanism, which pulls the sample vessel held at the plug-in site into the entry device, before the needle of the sample transport container is inserted into the sample vessel, thus avoiding any risk of injury by the needle and precluding premature removal of the sample vessel.

Typically the central axis of the sample vessel points upwards from the plug-in site and forms an angle of 30° to 40° with the horizontal plane, permitting the sample to be aspirated from a bubble-free region of the sample vessel.

In another embodiment of the invention, the entry device is provided with a typically optical monitoring unit in the area of the plug-in site for sample vessels, which serves to ascertain the correct positioning of the diverse sample vessels.

According to yet another embodiment, there may be provided at least one optical sensor in the interior of the entry device, for the purpose of monitoring the position of the sample transport container. If transparent sample transport containers are used, this sensor can also be employed to detect the presence of air or air bubbles in the sample.

These and other features and advantages of the present invention will be more fully understood from the following detailed description of the invention taken together with the accompanying claims. It is noted that the scope of the claims is defined by the recitations therein and not by the specific discussions of features and advantages set forth in the present description.

BRIEF DESCRIPTION OF THE DRAWINGS

The following detailed description of the embodiments of the present invention can be best, understood when read in conjunction with the following drawings, where like structure is indicated with like reference numerals and in which:

FIGS. 2 to 6 show parts of the device according to FIG. 1 in different operating states with an open sample vessel being used (e.g., a syringe) in accordance with an embodiment of the present invention;

FIGS. 7 to 9 show parts of the device according to FIG. 1 in different operating states with a closed sample vessel being used (e.g., a Vacutainers®) in accordance with an embodiment of the present invention;

Skilled artisans appreciate that elements in the figures are illustrated for simplicity and clarity and have not necessarily been drawn to scale. For example, the dimensions of some of the elements in the figures may be exaggerated relative to other elements to help improve understanding of the embodiment(s) of the present invention.

DETAILED DESCRIPTION OF THE INVENTION

The sample entry device 1 schematically shown in FIGS. 1 to 9 is used for the automated input of medical samples, typically samples of body fluids, or quality control media. In contrast to state-of-the-art entry devices diverse open and closed sample vessels 3, 4 may be used at a single plug-in site 2 of the device according to the invention.

Figure 1:
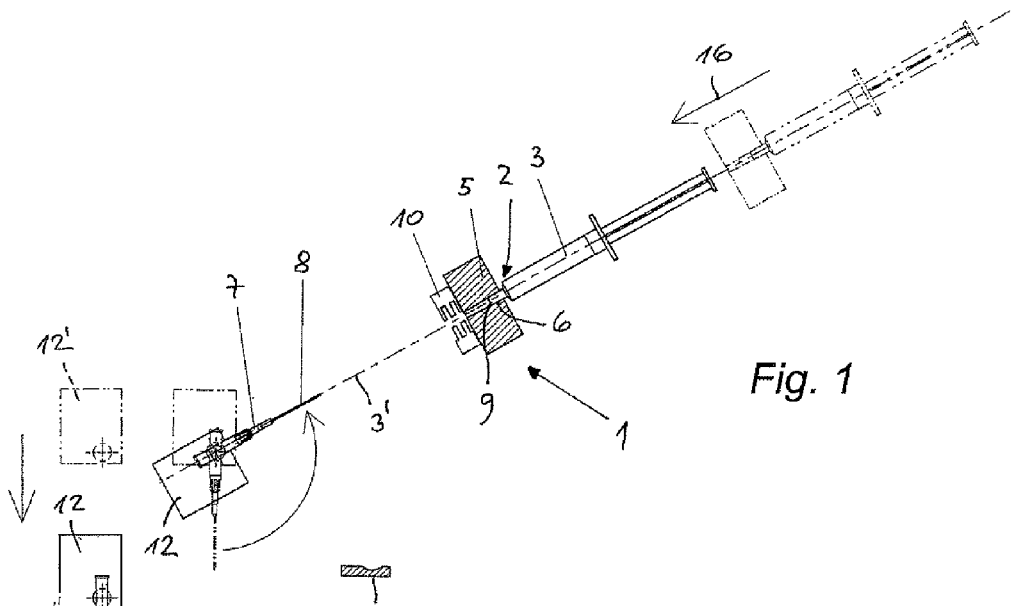
FIG. 1 gives a schematic view of a sample entry device according to an embodiment of the present invention.
Figure 2:
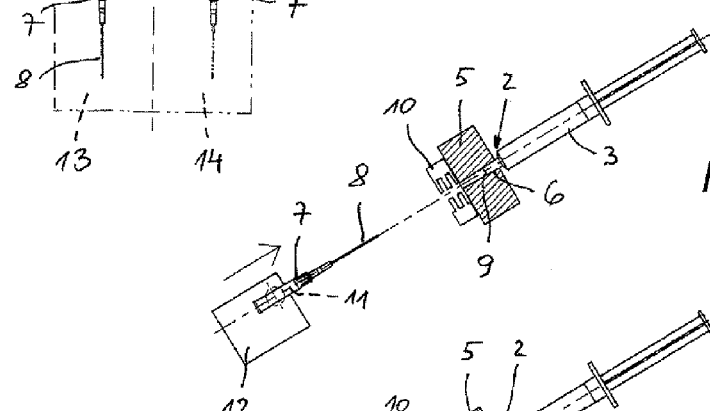
Figure 3:
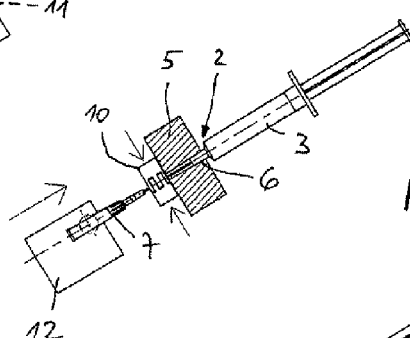
Figure 4:
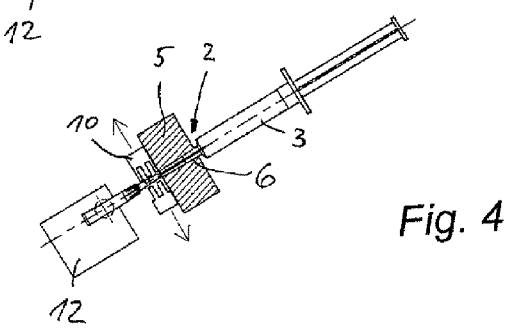

FIG. 1 shows an open sample vessel 3 (e.g., a syringe), which is held in place at the plug-in site 2 by means of a holding element 5. The open sample vessel 3 is inserted with its luer or Luer-Lok® connector into a suitably configured conical receptor 6 of the holding element 5, which receptor is part of a through-hole, and is fixed in the position defined by the holding element 5. Furthermore the entry device 1 is supplied with sample transport containers 7, each having a sharpened cannula 8, which can be introduced into the small-diameter opening 9 of the luer connector of the open sample vessel 3 by way of the through-hole of the holding element 5. The hollow needle (e.g., steel) of the cannula 8 has for instance an outer diameter of approximately 0.8 mm, thus necessitating very precise guiding (±0.2 mm) for inserting it successfully Into the small-diameter opening 9 of the open sample vessel 3 (inner diameter ca., 1.2 mm), i.e., for introducing the cannula 8 into the open sample vessel 3 without difficulties. For this purpose the entry device 1 is provided with guiding elements 10, which prior to insertion of the cannula 8 of the sample transport container 7, guide and center the cannula 8, aligning themselves on the center of the conical receptor 6 of the holding element 5, respectively on the luer connector (see FIG. 3).

The sample transport container 7 essentially consists of a body (e.g., plastic) with a hollow space 11 (see FIG. 2) for receiving the sample and on its entry side is provided with the cannula 8, or instance a hollow needle (e.g., steel) sharpened as a cannula. As indicated in FIG. 1 the sample transport container 7, which in accordance with one embodiment of the present invention is designed as a single-use element, is taken by a gripping and swiveling mechanism 12 from a storage space 13 indicated by broken lines, and is discarded after use into a waste space 14 also indicated by broken lines.

The gripping and swiveling mechanism 12 is shown in FIG. 1 in diverse positions. Departing from a position 12' shown by broken lines a sample transport container 7 is taken from the storage space 13. The sample transport container 7 is swivelled until its axis coincides with the axis 3' of the open sample vessel 3. By mutual translational movement of the open sample vessel 3 and the sample transport container 7 towards each other the cannula 8 is introduced into the interior of the open sample vessel 3 and the sample is withdrawn. Thereafter the sample is transferred to a sample entry or sample measuring site 15 (not shown in detail in the drawing), and the used sample transport container 7 is discarded into the waste space 14. Before the sharpened cannula 8 of the sample transport container 7 penetrates into the open sample vessel 3, the sample vessel 3 is retracted into the interior of the sample entry device 1, as indicated by the arrow 16 in FIG. 1, in order to avoid injury to the operator by the cannula 8 or premature removal of the open sample vessel 3 from the plug-in site 2.

As shown in detail in FIGS. 2 to 6, the sample transport container 7 with the cannula 8 is moved towards the opening 9 of the open sample vessel 3 (FIG. 2), then the guiding elements 10 close in order to facilitate insertion of the cannula 8 into the open sample vessel 3 (FIG. 3), and open again as soon as the cannula 8 has entered the open sample vessel 3 to avoid contamination of the guiding elements 10 by sample droplets possibly emerging when the cannula 8 penetrates into the open sample vessel 3 or when the cannula 8 is withdrawn after aspiration of the sample. After the aspiration process has ended the sample transport container 7 moves back into its initial position, is swivelled downwards through a certain angle β (FIG. 5) and transfers the sample for instance to a sample measuring site 15 (e.g., a test strip) (FIG. 6).

If a closed sample vessel 4 is used (e.g., a Vacutainer® or Monovette®) the sample vessel 4, which is closed by a lid element 17, e.g., a septum, is first placed into the plug-in site 2 of the entry device (see FIGS. 7 to 9), whereupon the closed sample vessel 4 is moved towards the sample transport container 7 by a retracting mechanism (see FIGS. 7 and 8). The closed sample vessel 4 is then firmly held at the plug-in site 2 by means of holding brackets 18. Subsequently the process of sample transfer takes place according to FIGS. 3 to 6, with the lid element 17 of the sample vessel being punctured by the cannula 8 of the sample transport container 7 and the sample being withdrawn from the closed sample vessel 4. As above, the sample transport container 7 together with cannula 8 is moved towards the lid element 17 of the closed sample vessel 4, then the guiding elements 10 close in order to facilitate penetration of the lid element 17 and insertion of the cannula 8 into the closed sample vessel 4 through the lid element 17, and to avoid bending of the cannula 8, and they are opened again after the cannula 8 has entered the closed sample vessel 45 to avoid contamination of the guiding elements 10 by possibly emerging sample droplets.

The central axis of the open and closed sample vessels 3, 4 points upwards departing from the plug-in site 2 and is inclined against the horizontal plane by an angle of about 30°, to permit the samples contained in the open and closed sample vessels 3, 4 to be aspirated free of air-bubbles. The closed sample vessel 4 (e.g., a Monovette®) may thus be positioned in the device before the holding brackets 18 grip.

Due to the fact that sample transport is carried out with a sample transport container 7 designed as a single-use item, and that the sample entry device 1 has no contact with the medical samples, cleaning or washing units are not required and there is no need for maintenance considerations in the design of the sample entry device 1. Holding and guiding elements are also free of contamination.

Figure 10:
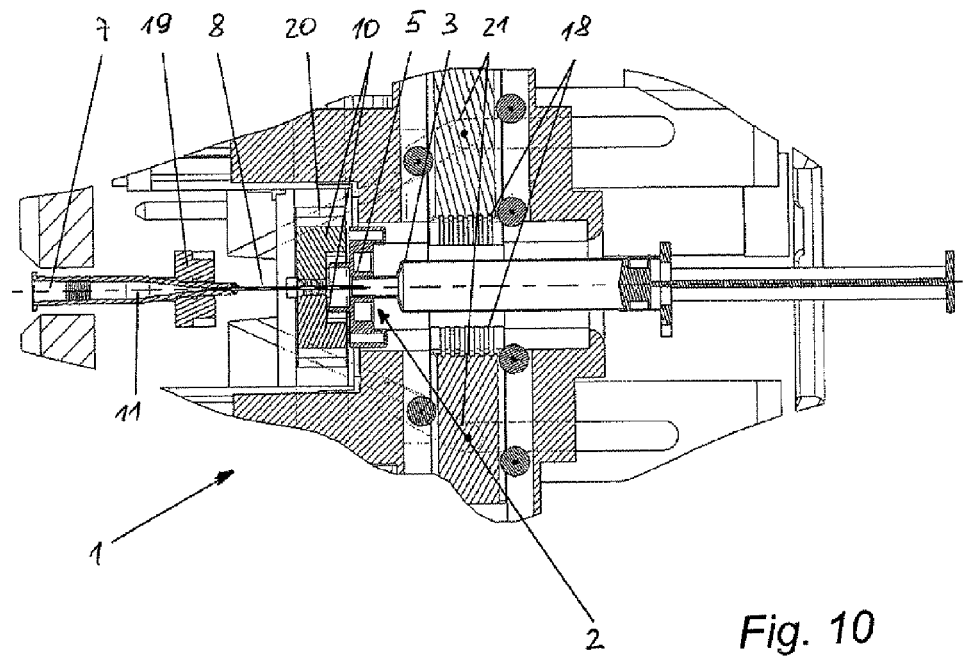
FIG. 10 shows a concrete embodiment of a sample entry device according to an embodiment of the present invention in a sectional view with an open sample vessel being used (e.g., a syringe)
Figure 11:
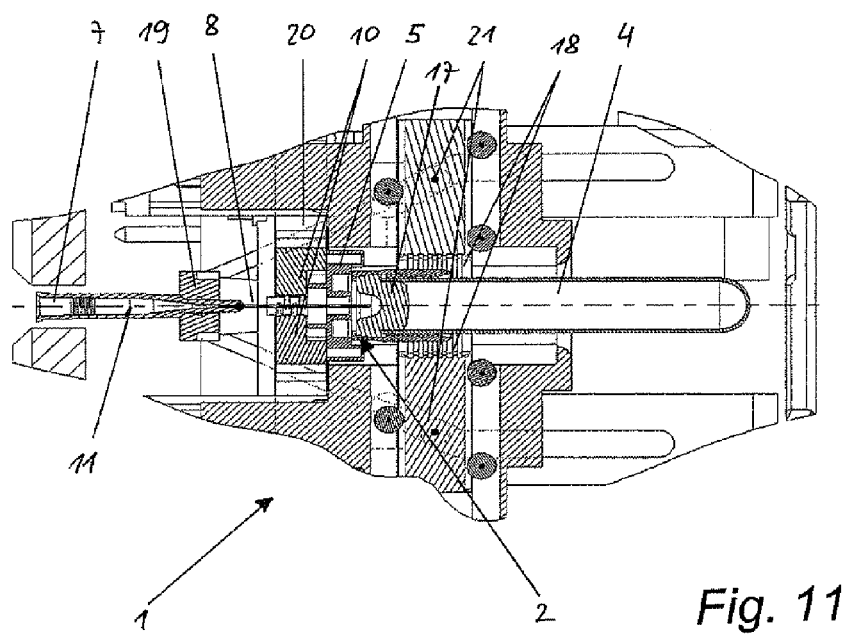
FIG. 11 shows a sample entry device as in FIG. 10 with a closed sample vessel being used (e.g., a Vacutainers®) in accordance with an embodiments of the present invention.

FIGS. 10 and 11 show an embodiment of the sample entry device 1 according to the present invention in a constructional drawing, with an open sample vessel 3 (e.g., a syringe), being plugged into the plug-in site 2 in FIG. 10. The luer connector of the open sample vessel 3 is held in the holding element 5; in the operational state shown in the drawing the open sample vessel 3 has already been pulled into the entry device 1. When an open sample vessel 3 is plugged into the device 1 the holding brackets 18, which may be electrically activated, are not used since they serve only for holding closed sample vessels 4, such as a closed sample vessel 4 as shown in FIG. 11, which is plugged into the site 2 of the sample entry device 1. Advantageously, the holding brackets 18 are guided by a link structure 21 and may thus be adapted to closed sample vessels 4 of different dimensions.

Before the cannula 8 is inserted into the open sample vessel 3 or through the lid element 17 into the closed sample vessel 4, it is centered and supported by the guiding elements 10. The guiding elements 10 are guided by a link structure 20 and may also be driven electrically.

In the area of the plug-in site 2 for open and closed sample vessels 3, 4 the sample entry device 1 may be provided with a typically optical monitoring unit (not further shown in the drawing), which serves to ascertain correct positioning of diverse open and closed sample vessels 3, 4. It is also possible to provide push-buttons or a touch-screen on the sample entry device 1, for manual entry of commands for the guiding elements 10, the holing brackets 18, or rather their electrical motors.

In the interior of the entry device 1 an optical sensor 19 may be provided, which serves for monitoring the positioning of the sample transport container 7. The sensor 19 can further be used to determine if the sample in the hollow space 11 of the sample transport container 7 has been aspirated tree of air-bubbles.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the invention in detail and by reference to specific embodiments thereof, it will be apparent that modifications and variations are possible without departing from the scope of the invention defined in the appended claims. More specifically, although some aspects of the present invention are identified herein as preferred or particularly advantageous, it is contemplated that the present invention is not necessarily limited to these preferred aspects of the invention.

What is claimed is:

1. A sample entry device comprising:
a single plug-in site for the automated input of samples from both open and closed sample vessels, wherein
a first, open sample vessel is open at one terminal end, and
a second, closed sample vessel is closed at both terminal ends, said closed sample vessel comprising a penetrable lid element at one said closed terminal end;
at least one sample transport container, each said sample transport container having a cannula, wherein said cannula is insertable through said open terminal end into said first, open sample vessel, and is also insertable through said penetrable lid element into said second, closed sample vessel; and
guiding elements configured to guide and/or center said cannula of said sample transport container in relation to said open terminal end or said penetrable lid element, wherein said guiding elements are configured to open and close, thereby actively gripping or passively guiding said cannula prior to insertion or penetration of the cannula into said open or closed sample vessel.

2. The sample entry device according to claim 1 further comprising holding elements for holding said open and said closed sample vessels at the single plug-in site.

3. The sample entry device according to claim 1, wherein the sample transport container has a body with a hollow space for receiving the sample and is provided on an entry side with a hollow needle sharpened as a cannula.

4. The sample entry device according to claim 1, wherein the sample transport container is configured as a single-use item.

5. The sample entry device according to claim 4, wherein a plurality of sample transport containers are held in a storage space of the sample entry device, and wherein a gripping and swiveling mechanism is provided, which takes a sample transport container from the storage space, aligns it for sample withdrawal from the sample vessel, inserts it into said sample vessel and, after the sample has been withdrawn and transferred, discards it into the storage space or into a separate waste space.

6. The sample entry device according to claim 2, wherein the holding element for holding open sample vessels has a conical receptor at the plug-in site.

7. The sample entry device according to claim 1, wherein said open sample vessel is a syringe.

8. The sample entry device according to claim 1 further comprising holding brackets for holding said closed sample vessels in position at the plug-in site.

9. The sample entry device according to claim 8, wherein the holding brackets are guided by a link structure and thus are adjustable to different dimensions of closed sample vessels.

10. The sample entry device according to claim 1, wherein the central axis of the sample vessel points upward starting from the plug-in site, and forms an angle of 30° to 40° with the horizontal plane.

11. The sample entry device according to claim 1 further comprising one or more monitoring units which detect the position of the open or closed sample vessel or sample transport container.

12. The sample entry device according to claim 11, wherein said monitoring unit is optical.

13. The sample entry device according to claim 11, wherein said monitoring unit further detects the presence of air or air bubbles in the sample.

14. A sample entry device comprising:
a single plug-in site for the automated input of samples from both open and closed sample vessels, wherein
a first, open sample vessel is open at one terminal end, and
a second, closed sample vessel is closed at both terminal ends, said closed sample vessel comprising a penetrable lid element at one said closed terminal end;
at least one sample transport container, each said sample transport container having a cannula, wherein said cannula is insertable through said open terminal end into said first, open sample vessel, and is also insertable through said penetrable lid element into said second, closed sample vessel;
guiding elements configured to actively grip or passively guide said cannula of said sample transport container prior to insertion or penetration of the cannula into said open or closed sample vessel to guide and/or center the cannula; and
a retracting mechanism, which pulls the sample vessels held in position at the plug-in site into the entry device.

15. A sample entry device comprising:
a single plug-in site for the automated input of samples from both open and closed sample vessels, wherein
a first, open sample vessel is open at one terminal end, and
a second, closed sample vessel is closed at both terminal ends, said closed sample vessel comprising a penetrable lid element at one said closed terminal end;
at least one sample transport container, each said sample transport container having a cannula, wherein said cannula is insertable through said open terminal end into said first, open sample vessel, and is also insertable through said penetrable lid element into said second, closed sample vessel; and
guiding elements configured to actively grip or passively guide said cannula of said sample transport container prior to insertion or penetration of the cannula into said open or closed sample vessel to guide and/or center the cannula, wherein the guiding elements for centering the cannula of the sample transport container will grip the cannula prior to insertion of the cannula into said open sample vessel or penetration of said lid element of said closed sample vessel.

16. The sample entry device of claim 15, wherein the guiding elements are configured to open once the cannula has entered the open or the closed sample vessel.

\* \* \* \* \*